US010166055B2

(12) United States Patent
Eekhoff et al.

(10) Patent No.: US 10,166,055 B2
(45) Date of Patent: Jan. 1, 2019

(54) METHOD AND APPARATUS FOR BONE FIXATION

(71) Applicant: BIOMET C.V., Gibraltar (GI)

(72) Inventors: Jeremy Eekhoff, Holland, MI (US); Joseph M. O'Reilly, Granger, IN (US)

(73) Assignee: Biomet C.V., Warsaw, IN (US)

( * ) Notice: Subject to any disclaimer, the term of this patent is extended or adjusted under 35 U.S.C. 154(b) by 521 days.

(21) Appl. No.: 14/279,398

(22) Filed: May 16, 2014

(65) Prior Publication Data

US 2015/0327902 A1 Nov. 19, 2015

(51) Int. Cl.
*A61B 17/86* (2006.01)
*A61B 17/88* (2006.01)
*A61B 17/72* (2006.01)
*A61B 17/80* (2006.01)
*A61B 17/68* (2006.01)

(52) U.S. Cl.
CPC ........ *A61B 17/8685* (2013.01); *A61B 17/862* (2013.01); *A61B 17/8891* (2013.01); *A61B 17/725* (2013.01); *A61B 17/80* (2013.01); *A61B 17/864* (2013.01); *A61B 17/8625* (2013.01); *A61B 2017/681* (2013.01)

(58) Field of Classification Search
CPC ................... A61B 17/68; A61B 17/84–17/864
USPC ........................................................ 606/304
See application file for complete search history.

(56) References Cited

U.S. PATENT DOCUMENTS

| 4,456,005 A * | 6/1984 | Lichty | A61B 17/8685 606/315 |
| 4,940,467 A * | 7/1990 | Tronzo | A61B 17/742 606/304 |
| 5,100,405 A * | 3/1992 | McLaren | A61B 17/72 606/304 |
| 5,498,265 A * | 3/1996 | Asnis | A61B 17/74 606/315 |
| 5,827,285 A * | 10/1998 | Bramlet | A61B 17/68 411/166 |
| 5,961,329 A * | 10/1999 | Stucki-McCormick | A61B 17/666 433/173 |
| 6,093,207 A | 7/2000 | Pisharodi | |
| 6,319,254 B1 | 11/2001 | Giet et al. | |
| 7,582,107 B2 | 9/2009 | Trail et al. | |
| 7,938,836 B2 * | 5/2011 | Ainsworth | A61B 17/025 606/99 |

(Continued)

Primary Examiner — Zade Coley
(74) Attorney, Agent, or Firm — Schwegman Lundberg & Woessner, P.A.

(57) ABSTRACT

A fastener assembly can include a proximal fastener member, a distal fastener member and an internal fastener member. The proximal fastener can include a fastener head and an internal wall defining an anti-rotation feature. The distal fastener can include a proximal end defining an internal bore and an external anti-rotation feature, and a distal end defining a bone anchor. The internal fastener can be positioned in the cannulated proximal fastener and threadably coupled to the distal fastener such that the proximal end of the distal fastener is telescopically received in a distal end of the proximal fastener. Rotation of the internal fastener in a first rotational direction can telescopically retract the distal fastener into the proximal fastener so as to be adapted to compress a bone fracture. Rotation of the internal fastener in an opposite rotational direction can extend the distal fastener relative to the proximal fastener.

13 Claims, 13 Drawing Sheets

(56) References Cited

U.S. PATENT DOCUMENTS

| | | |
|---|---|---|
| 8,308,783 B2 | 11/2012 | Morris et al. |
| 8,343,200 B2 | 1/2013 | Khanna et al. |
| 8,394,103 B2 | 3/2013 | O'Reilly et al. |
| 8,715,326 B2 * | 5/2014 | Champagne ....... A61B 17/7225 606/104 |
| 2001/0000186 A1 | 4/2001 | Bramlet et al. |
| 2001/0049528 A1 * | 12/2001 | Kubota ................ A61B 17/742 606/65 |
| 2003/0069582 A1 * | 4/2003 | Culbert ................ A61B 17/68 606/65 |
| 2007/0118132 A1 * | 5/2007 | Culbert ............. A61B 17/7064 606/279 |
| 2008/0294164 A1 | 11/2008 | Frank et al. |
| 2009/0069813 A1 * | 3/2009 | von Hoffmann ...... A61B 17/68 606/65 |
| 2011/0319946 A1 | 12/2011 | Levy et al. |
| 2013/0116694 A1 | 5/2013 | Zurschmiede |
| 2013/0317503 A1 * | 11/2013 | Songer ................ A61B 17/742 606/66 |

\* cited by examiner

METHOD AND APPARATUS FOR BONE FIXATION

FIELD

The present disclosure relates generally to a method and apparatus for bone fixation and, more particularly, to bone fracture fixation.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical or medical procedures are often performed on a body, for example, a human body or anatomy, to repair or replace various portions thereof. For example, after trauma, there may be a need to fix bone fragments together to immobilize the fragments and permit healing. Compressive force can be applied to the bone fragments to compress them together such that upon ingrowth of new bone, the fragments will heal together and restore strength to the trauma site. Conventional compression screws can be utilized to compress the bone fragments together, but are often required to be introduced from both or opposed sides of the bone to sufficiently compress the fracture to assure proper healing. Accordingly, while such compression screws work for their intended purpose, there remains a need for improvement in the relevant art.

SUMMARY

This section provides a general summary of the disclosure, and is not a comprehensive disclosure of its full scope or all of its features.

In one form, a fastener assembly for use with fracture fixation is provided in accordance with various aspects of the present disclosure. In an exemplary implementation, the fastener assembly can include a cannulated proximal fastener member, a distinct distal fastener member and a distinct internal fastener member. The proximal fastener member can include a proximal fastener head, an opposed distal end and an internal wall defining an internal anti-rotation feature. The distal fastener member can include a proximal end defining an internal bore and an external anti-rotation feature, and a distal end defining a bone anchor. The internal fastener member can be configured to be positioned in the proximal fastener member and can be threadably coupled to the distal fastener member such that the proximal end of the distal fastener member can be telescopically received in the distal end of the cannulated proximal fastener member. Rotation of the internal fastener member in a first rotational direction can telescopically retract the distal fastener member into the proximal fastener member so as to be adapted to compress a bone fracture. Rotation of the internal fastener member in a second opposite rotational direction can extend the distal fastener member relative to the proximal fastener member.

In some implementations, the fastener assembly can include a retention arrangement configured to prevent axial movement of the internal fastener member relative to the proximal fastener member while allowing relative rotation movement of the internal fastener member. In these implementations, the retention arrangement can include one or more apertures defined by the proximal fastener member adjacent to the proximal head; one or more retention members configured to be positioned in the corresponding one or more apertures; and an annular recess defined by a head of the internal fastener member. The one or more retention members positioned in the one or more apertures can be received in the annular recess, thereby preventing axial movement of the internal fastener member relative to the proximal fastener member while allowing relative rotation movement of the internal fastener member.

In another form, a fracture fixation system is provided in accordance with various aspects of the present disclosure. In an exemplary implementation, the fracture fixation system can include a fastener assembly and an instrument assembly. The fastener assembly can include a cannulated proximal fastener member, a distinct distal fastener member and a distinct internal fastener member. The proximal fastener member can have a fastener head, an opposed distal end and an internal wall defining an anti-rotation feature. The distal fastener member can have a proximal end defining a threaded internal bore and an external anti-rotation feature, and a distal end defining a bone anchor. The internal fastener member can be configured to be positioned in the proximal fastener member and can be threadably coupled to the distal fastener member such that the distal fastener member can be telescopically received in the proximal fastener member. The instrument assembly can include a cannulated first instrument and a cannulated second driver. The first instrument can have a first handle at a proximal end and a first distal end configured to be removably coupled to a first coupling feature defined by the fastener head. The second driver can be configured to be removably positioned in the first instrument and can have a second distal end defining a second drive feature configured to be removably coupled to a second coupling feature defined by the fastener head.

In some implementations, a third driver can be configured to be removably received in the second driver and can have a third distal end defining a third drive feature configured to be removably coupled to a third coupling feature defined by the internal fastener member. In accordance with various aspects of the present teachings, rotation of the internal fastener member by the third driver relative to the first instrument and second driver in a first rotational direction can telescopically retract a proximal end of the distal fastener member into a distal end of the proximal fastener member so as to be adapted to compress a bone fracture.

In yet another form, a method for use with fracture fixation is provided in accordance with various aspects of the present disclosure. In an exemplary implementation, the method can include forming a hole in a bone having a fracture. A first instrument can be coupled to a proximal head of a fastener assembly. The fastener assembly can include a proximal fastener member having the proximal head, a distal fastener member telescopically received in the proximal fastener member and an internal fastener member positioned in the proximal fastener member and threadably coupled to the distal fastener member. The fastener assembly can be advanced into the bone hole and can be threadably secured to the bone with the first instrument. A driver can be positioned into the first instrument and the driver can be coupled to the internal fastener member. The driver can be rotated to rotate the internal fastener member and telescopically retract the distal fastener member into the proximal fastener member to compress the fracture.

In some implementations, forming the hole in the bone having the fracture can include forming the hole in a femur from only a lateral side of the femur having an intercondylar fracture. In some implementations, forming the hole in the femur from only the lateral side of the femur can include forming one or more bone holes in the femur only from the lateral side to compress the intercondylar fracture. In some implementations, a proximal head driver can be inserted into the cannulated first instrument and a distal end of the proximal head driver can be coupled to a drive coupling feature defined by the proximal head.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

Figure 10:
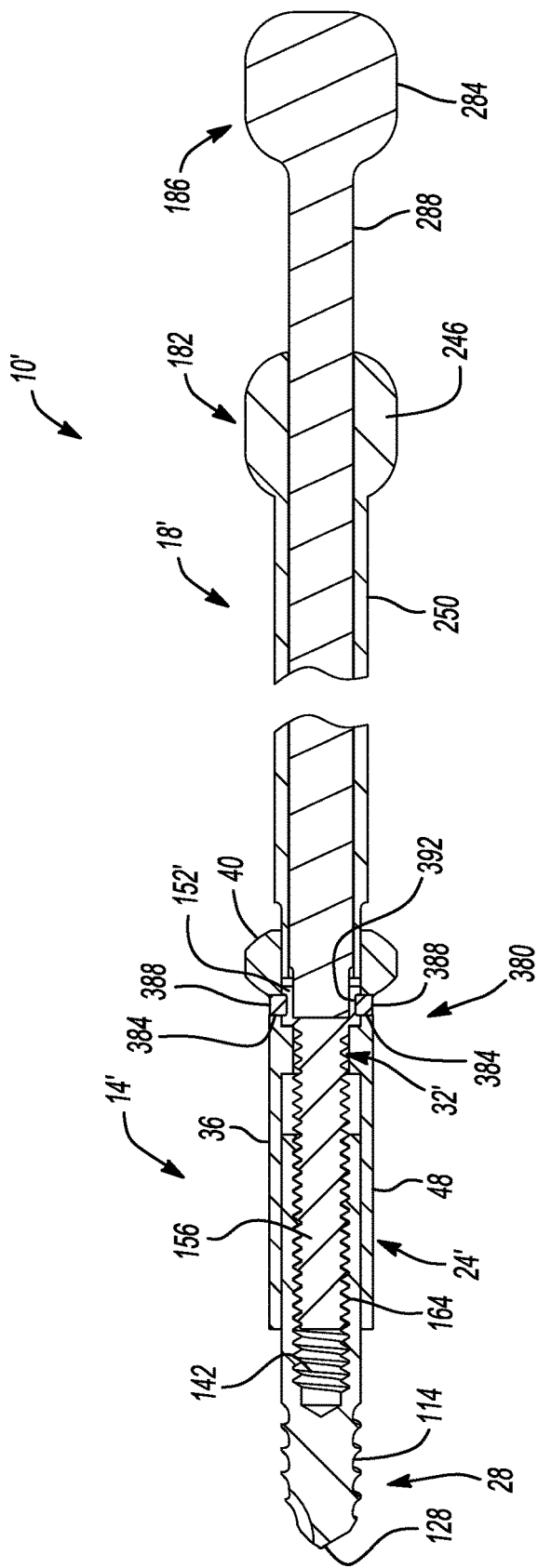
FIG. 10 is a sectional view of an exemplary fastener assembly associated with an exemplary instrument assembly according to various aspects of the present disclosure.
Figure 11:
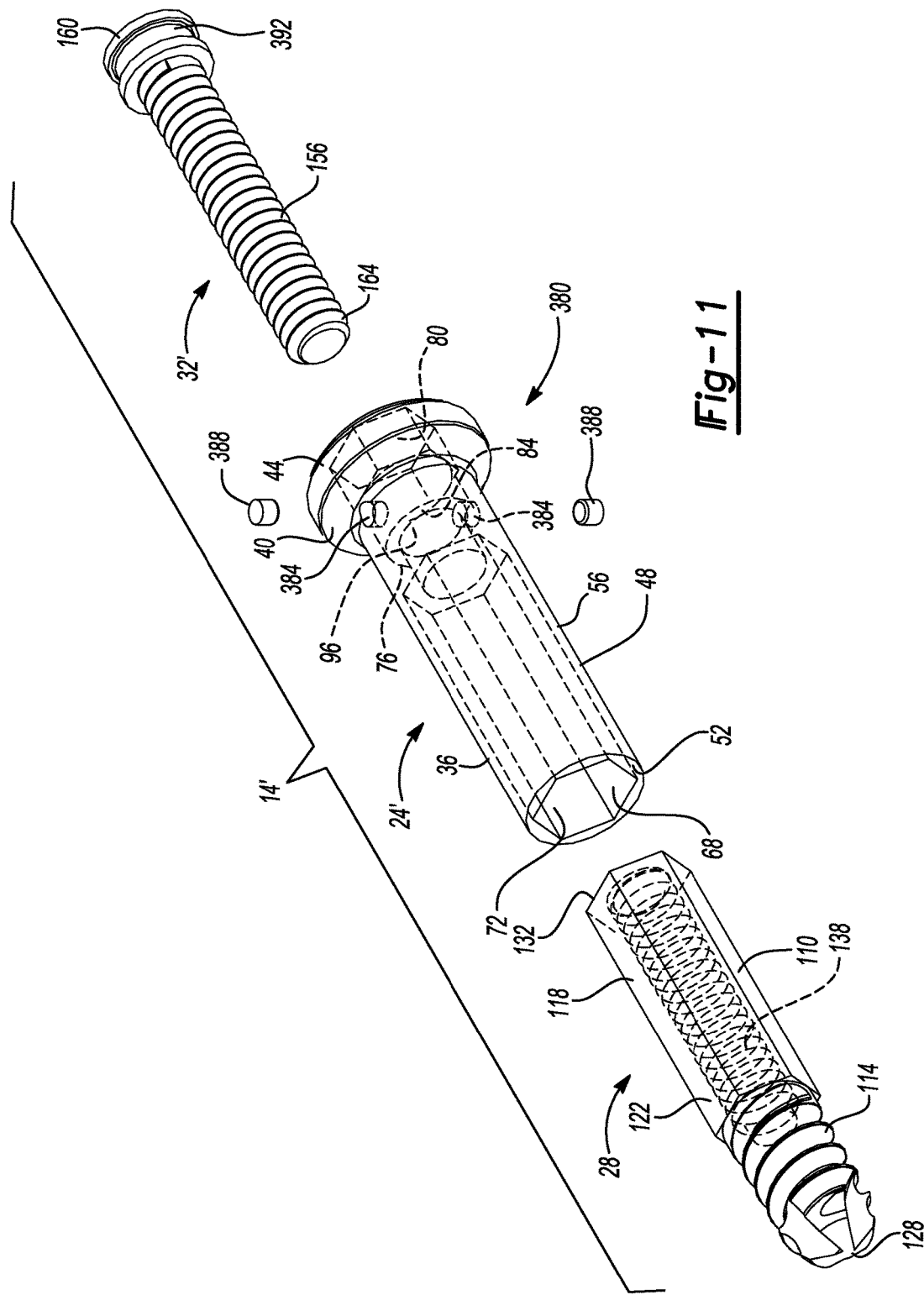
FIG. 11 is an exploded view of the fastener assembly of FIG. 10 according to various aspects of the present disclosure.
Figure 12:
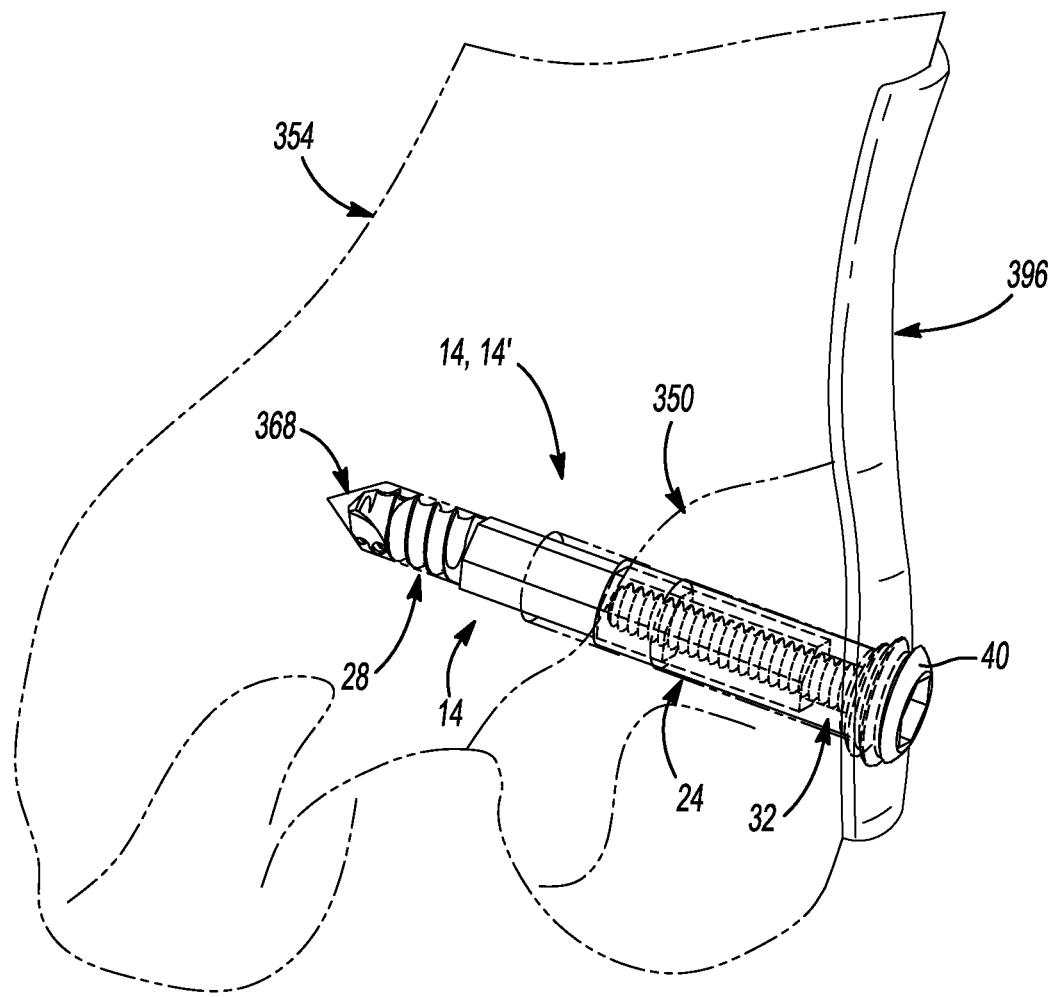
Figure 13:
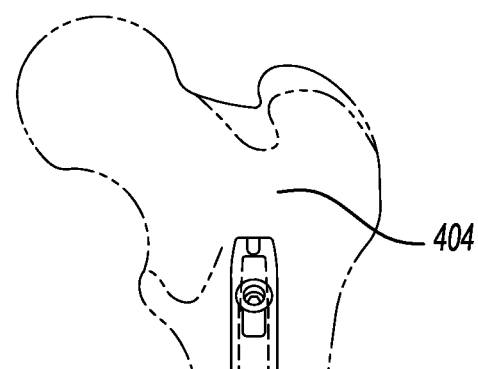
Figure 13:
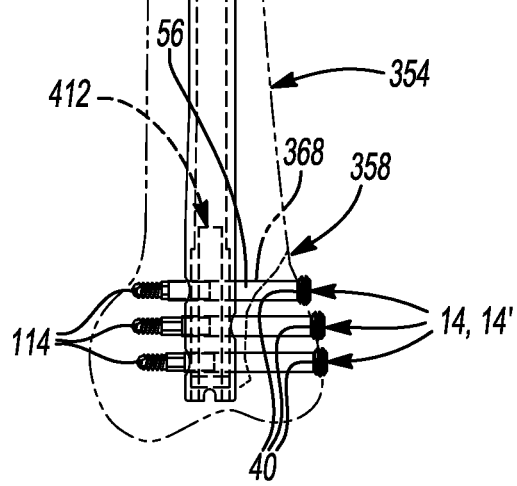

FIG. 12 depicts an exemplary system and method of fracture fixation using the instrument assemblies, fastener assemblies and techniques of FIGS. 7-11 with an exemplary bone plate according to various aspects of the present disclosure; and FIG. 13 depicts an exemplary system and method of fracture fixation using the instrument assemblies, fastener assemblies and techniques of FIGS. 7-11 with an exemplary orthopedic fastener system according to various aspects of the present disclosure.

DETAILED DESCRIPTION

The following description is merely exemplary in nature and is not intended to limit the present disclosure, its application, or uses. Although the following description is related generally to methods and apparatus for bone fracture fixation in a femur, it should be appreciated that the methods and apparatus discussed herein can be applicable to various bones and/or joints of the anatomy and can be utilized with various fixation systems and/or devices.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The present teachings provide fracture fixation systems and methods for using the same to facilitate bone fracture fixation and healing. In an exemplary aspect, the fracture fixation system includes an instrument assembly and an associated fastener assembly. In one exemplary aspect, the fastener assembly includes a compression screw assembly configured to facilitate bone fracture fixation and healing using only lateral access to the fractured bone. In an exemplary aspect, the fastener assembly can be utilized to compress an intercondylar fracture of a femur though only lateral access to femur. In another exemplary aspect, the instrument assembly and associated fastener assembly can be utilized with a bone plate and/or an orthopedic fixation system, such as an intramedullary nail, to facilitate bone fracture fixation.

With initial reference to FIGS. 1-5B, an exemplary fracture fixation system according to various aspects of the present teachings is shown and generally identified at reference numeral 10. As will be discussed in greater detail below, the fracture fixation system 10 can, in one exemplary implementation, provide for compression of an intercondylar fracture using only lateral access to the femur. In one exemplary aspect, the fracture fixation system 10 can include a fastener assembly 14 removably coupled to an instrument or inserter assembly 18. As will also be discussed in greater detail below, the fracture fixation system 10 can be provided as a kit including various different sizes and/or configurations of fastener assemblies 14 packaged with the instrument assembly 18.

The fastener assembly 14 can include a first or proximal fastener member 24, a second or distal fastener member or tip 28 and a third or internal screw or fastener member 32, as shown for example in FIGS. 2 and 4-5B. The proximal fastener member 24 can include a cannulated body 36 defining a cannulated proximal head 40 at a first or proximal end 44 and a cannulated shaft or shank portion 48 extending from the head 40 to an opposed second or distal end 52. In one exemplary implementation, the cannulated shaft 48 can include a smooth or substantially smooth outer cylindrical surface 56. The proximal head 40 can include, in one exemplary implementation, external threads 60 configured to be selectively removably coupled to the instrument assembly 18, as will be discussed in greater detail below.

The cannulated body 36 defines an internal wall 68 having an anti-rotation feature 72 associated with the shaft 48, a shoulder or reduced diameter portion 76 proximate the head 40 and an instrument coupling feature 80 at the head 40. In one exemplary implementation, the anti-rotation feature 72 includes an internal key feature, such as an exemplary hexagon or partial hexagon pattern shown in FIG. 5A. The anti-rotation feature 72 can extend, in one exemplary implementation, from the distal end 52 to the shoulder 76. It will be appreciated, however, that the anti-rotation feature 72 can extend along only a portion of the shaft 48, such as from the distal end 52 only partially toward the shoulder 76. It will also be appreciated that the anti-rotation feature can take other forms, such as a partial hexagon pattern or other suitable patterns or geometries configured to prevent relative rotation of mating components.

The shoulder or reduced diameter portion 76 can be formed proximate the head 40, but sufficiently recessed from the proximal end 44 to receive a head of the internal screw 32 below the instrument coupling feature 80 so as to not interfere with the instrument assembly 18 when coupled to the proximal fastener member 24. In the exemplary implementation illustrated in FIG. 5A, the reduced diameter portion 76 can include a stepped configuration 84 defining a first internal wall 88 and a shoulder or bearing surface 92 configured to bear against the head of the internal screw 32. The bearing surface 92 can define an aperture 96 for receiving a shank of the internal screw 32 therethrough, as will be discussed in greater detail below.

The internal wall 68 can define the instrument coupling feature 80 at the proximal head 40. In one exemplary implementation, the instrument coupling feature 80 can include an internal pattern configured to non-rotatably receive a drive feature of the instrument assembly 18 for driving and/or preventing rotation of the proximal fastener member 24, as will also be discussed in greater detail below. In the exemplary implementation shown in the various Figures, the instrument coupling feature 80 can include an internal hexagon pattern 102. In one exemplary implementation, the hexagon pattern 102 of the instrument coupling feature 80 can be sized and shaped to be the same or substantially the same as the hexagon pattern of the anti-rotation feature 72 to reduce manufacturing cost and complexity.

Figure 2:
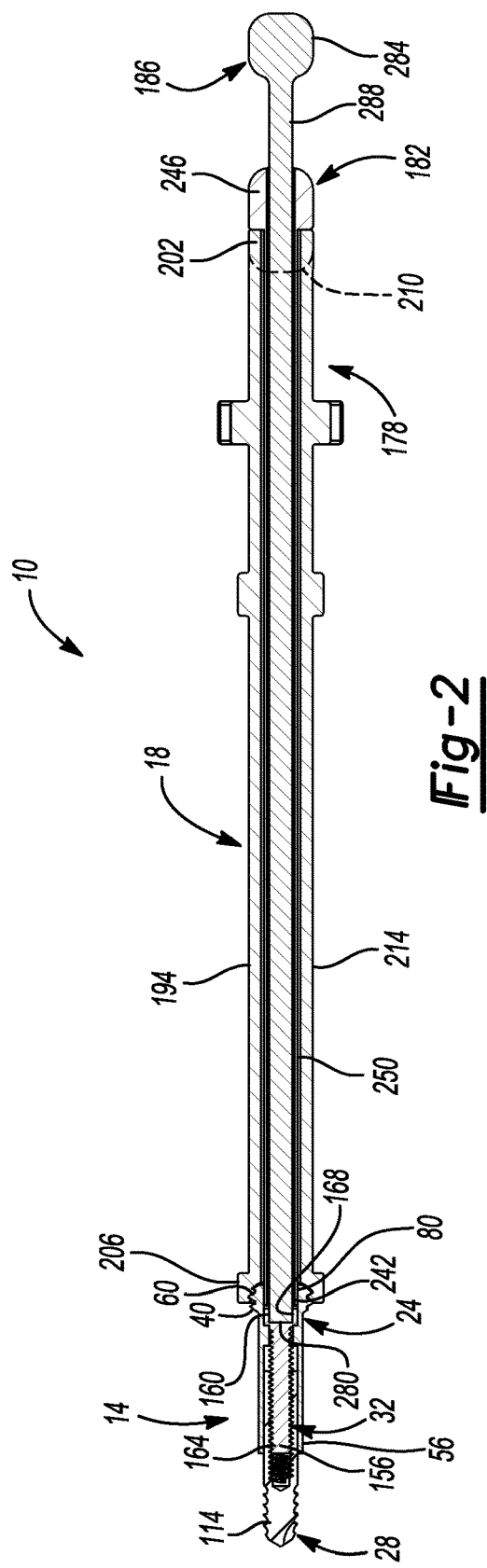
FIG. 2 is a sectional view of the fastener and instrument assemblies of FIG. 1 according to various aspects of the present disclosure.
Figure 3:
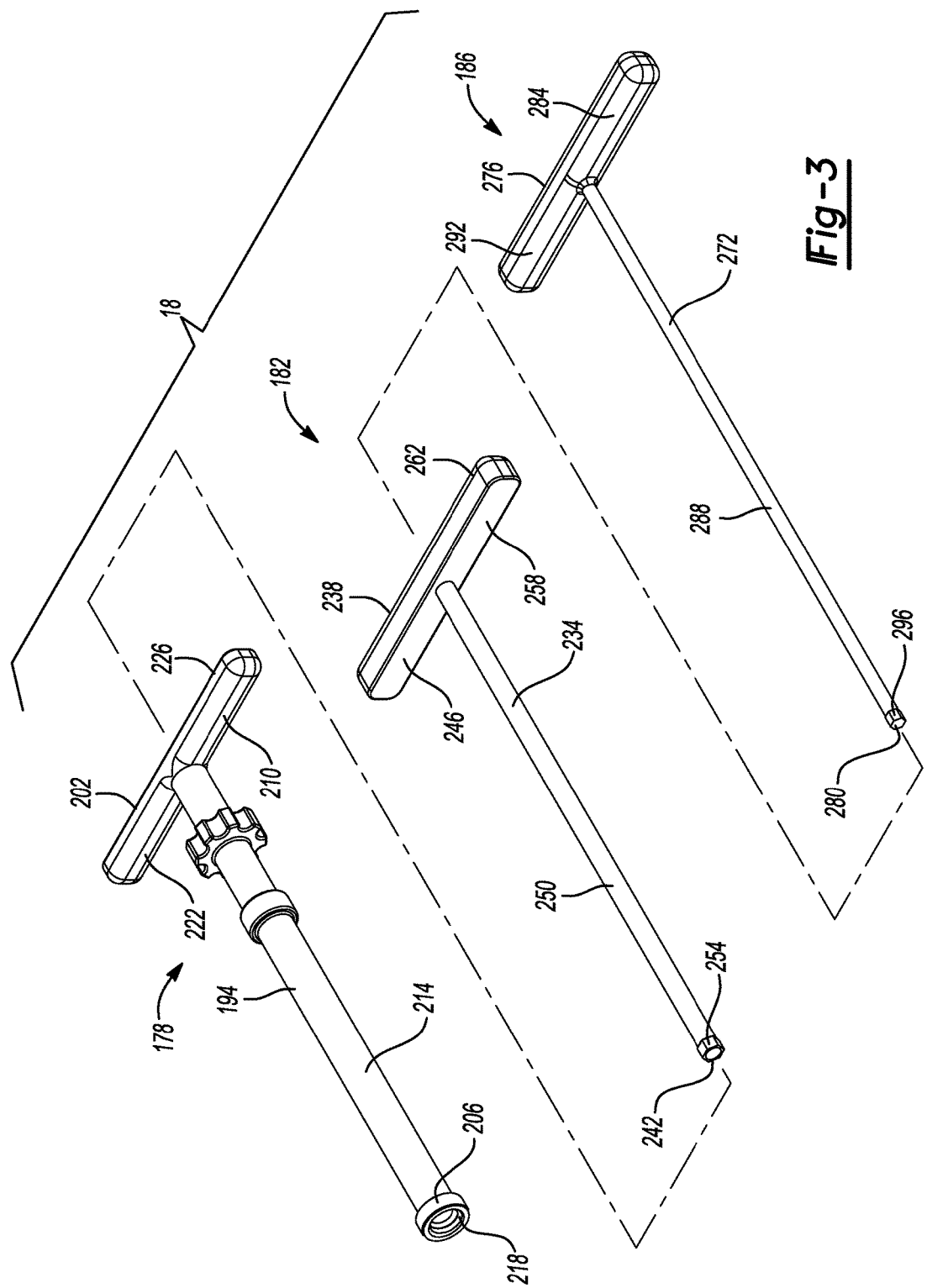
FIG. 3 is an exploded view of the instrument assembly of FIG. 1 according to various aspects of the present disclosure.
Figure 4:
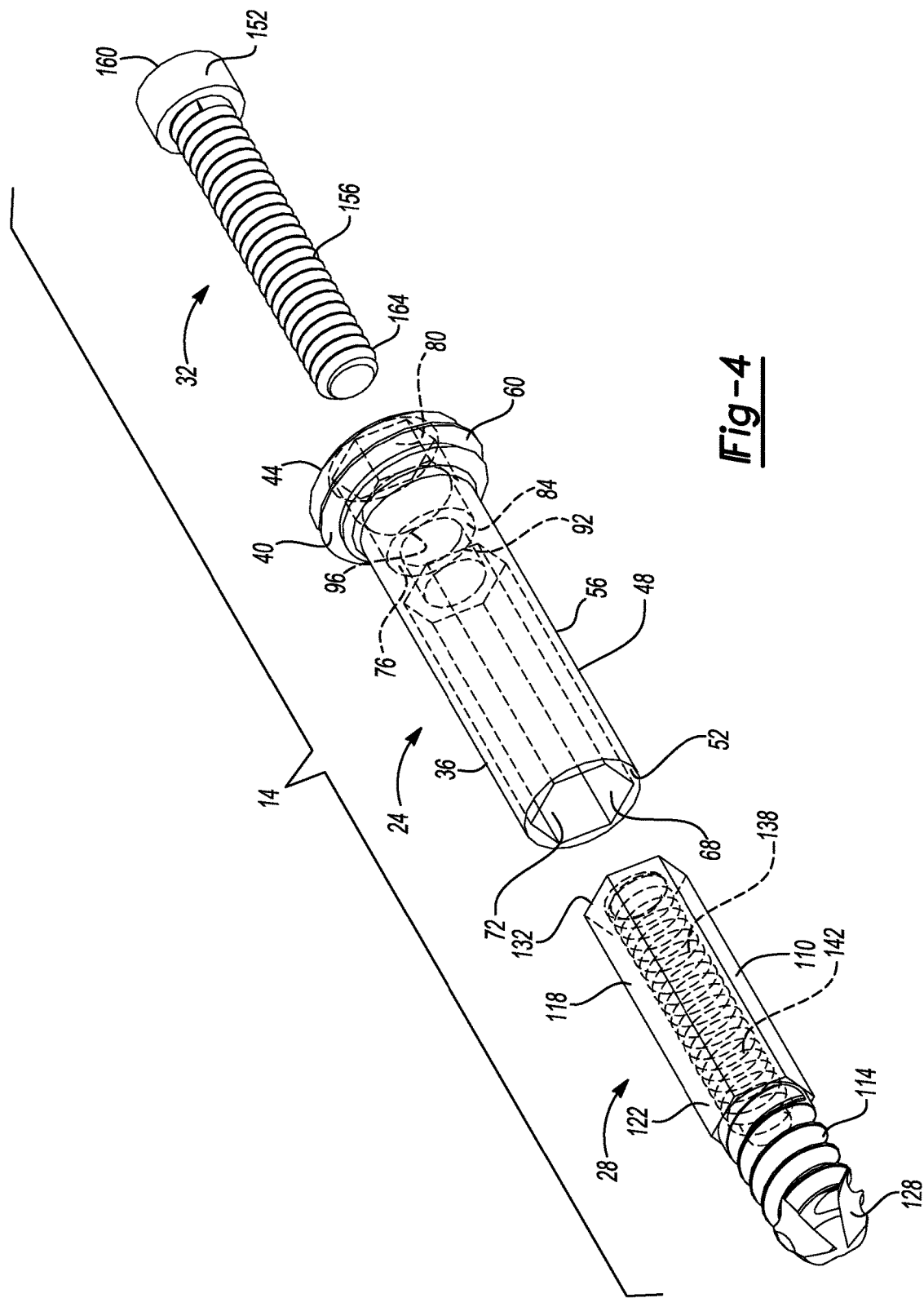
FIG. 4 is an exploded view of the fastener assembly of FIG. 1 according to various aspects of the present disclosure.
Figure 5A:
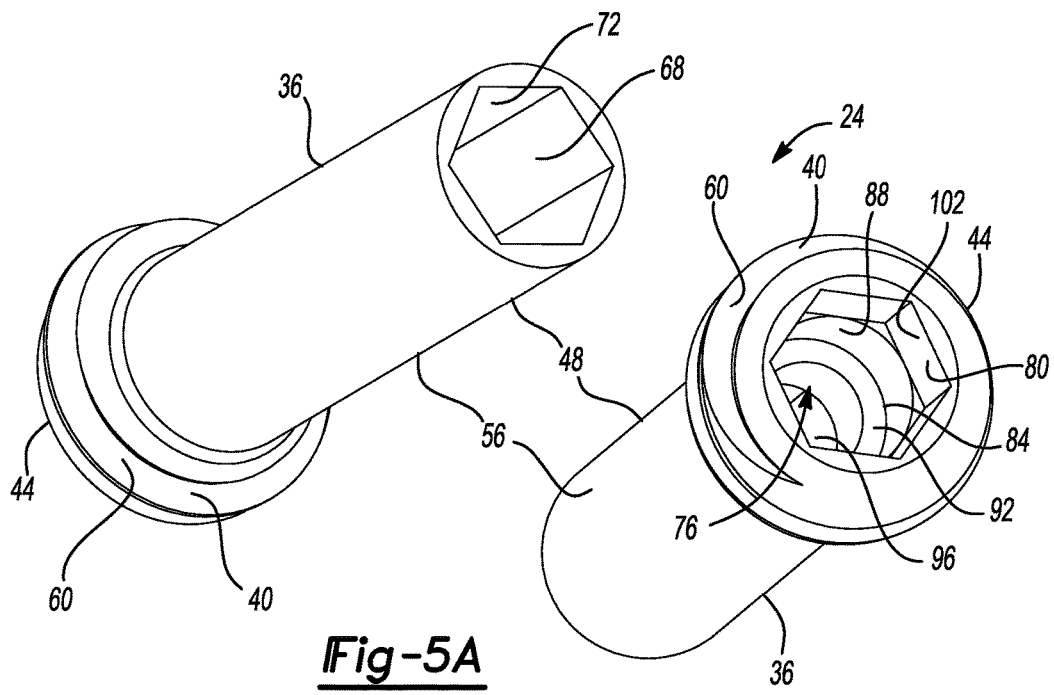
FIG. 5A illustrates perspective views of a proximal member of the fastener assembly according to various aspects of the present disclosure.
Figure 5B:
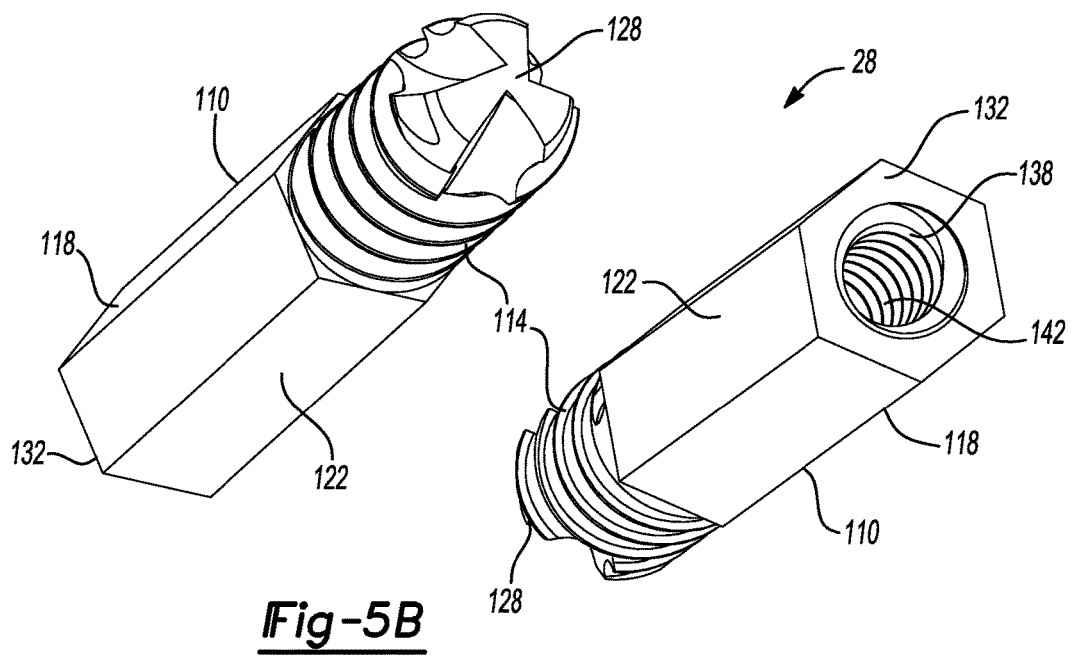
FIG. 5B illustrates perspective views of a distal member of the fastener assembly according to various aspects of the present disclosure.

With particular reference to FIGS. 4 and 5B and continuing reference to FIGS. 1-3 and 5A, the distal fastener member 28 will now be discussed in greater detail. As can be seen in FIG. 4 with reference to FIG. 2, the distal fastener member 28 can be configured to be telescopically received in the cannulated shaft 48 of the proximal fastener member 24 for controlled axial movement relative thereto. The distal fastener member 28 can include a body 110 defining a bone anchor distal end portion 114 and an upper or proximal member receiving portion 118 having an anti-rotation feature 122. In one exemplary implementation, the bone anchor portion 114 can include a threaded lower or distal end portion. In this exemplary implementation, the threaded distal end portion 114 can extend from a distal end or tip 128 to the anti-rotation feature 122, which can extend to a proximal end 132.

In the exemplary implementation illustrated, the bone anchor end portion 114 can include external threads configured to be secured to bone. The external threads can be configured to be utilized with a pre-formed bone hole and/or can be self-tapping threads. The anti-rotation feature 122 can be sized and shaped to be complementary to the anti-rotation feature 72 of the proximal fastener member 24 such that the proximal member receiving portion 118 can be non-rotatably telescopically received in the cannulated shaft 48 of the proximal fastener member 24, as shown for example in FIGS. 2 and 4. In other words, the anti-rotation features 72, 122 can include complementary surfaces that allow relative axial movement while preventing relative rotational movement. The body 110 of distal fastener member 28 can also define an internal blind bore 138 having internal threads 142 configured to threadably receive a threaded shaft of the internal screw 32, as will be discussed below in greater detail.

The internal fastener member or screw 32 can include a proximal head 152 and a threaded shaft 156 extending therefrom. The proximal head 152 can define an internal instrument coupling feature 168, such as an internal recessed hexagon pattern generally shown in FIG. 2. With particular reference to FIGS. 2, 4 and 5A-5B, assembly and general operation of the fastener assembly 14 will now be discussed in greater detail. The internal fastener member 32 can be received in the proximal fastener member 24 via the proximal end 44 such that the proximal head 152 rests on or engages the bearing surface 92. As briefly discussed above, the proximal head 152 can be sized and shaped together with the shoulder portion 76 such that an upper or top surface 160 of head 152 is below a bottom surface of the instrument coupling feature 80 of proximal head 40, as generally shown in FIG. 2.

In the exemplary implementation illustrated, the threaded shaft 156 can include an axial length sized such that when positioned in the proximal fastener member 24, a distal end portion 164 can extend to approximately the distal end 52 of proximal fastener member 24. This distal end portion 164 can be used, for example, to facilitate coupling the distal fastener member 28 to internal fastener member 32. The distal end portion 164 can also provide sufficient threaded engagement of the distal fastener member 28 to the internal fastener member 32 when the proximal end 132 of the distal fastener member 28 is adjacent the distal end 52 of the proximal fastener member 24. It will be appreciated, however, that the threaded shaft 156 of internal screw member 32 can have varying axial lengths including a length sized such that the distal end portion 164 extends beyond the distal end 128 of distal fastener member 28.

With the internal fastener member 32 positioned in or partially positioned in proximal fastener member 24, the distal end portion 164 can be threadably engaged to the internal threads 142 of distal fastener member 28. In one example, the proximal end 132 of distal fastener member 28 can be partially inserted into the cannulated shaft 48 of proximal fastener member 24 and the internal fastener member 32 can be rotated to threadably engage the threaded shaft 156 to the internal threads 142. Once the internal fastener member 32 is positioned in the proximal fastener member 24 and threadably engaged to the distal fastener member 28, rotation of the internal screw can vary the axial position of the distal fastener member 28 relative to the proximal fastener member 24.

In other words, the anti-rotation features 72 and 122 can cooperate to facilitate telescoping axial movement of the distal fastener member 28 relative to the proximal fastener member 24 with rotation of the internal screw 32. For example, clockwise rotation of the internal screw 32 can draw the distal fastener member 28 telescopically into the proximal fastener member 24 (e.g., towards the head 40 of proximal fastener member 24) since the anti-rotation features 72, 122 prevent relative rotation. Similarly, counterclockwise rotation of internal screw 32, in this example, can extend the distal fastener member 28 axially away from proximal member head 40 due to the anti-rotation features 72, 122 preventing relative rotation.

As will be discussed in greater detail below with reference to exemplary fracture fixation techniques utilizing the exemplary fastener fixation system 10, the fastener assembly 14 can be inserted into a fractured bone or bones in an axially extended configuration and, once secured to the bone(s), the internal fastener member 32 can be rotated to telescopically retract the distal fastener member 28 thereby shortening the fastener assembly 14 and compressing the fractured bone(s) to promote healing. The exemplary instrument assembly 18 can be utilized to insert the fastener assembly 14 into the bone(s) and control movement of the components of fastener assembly 14.

Figure 1:
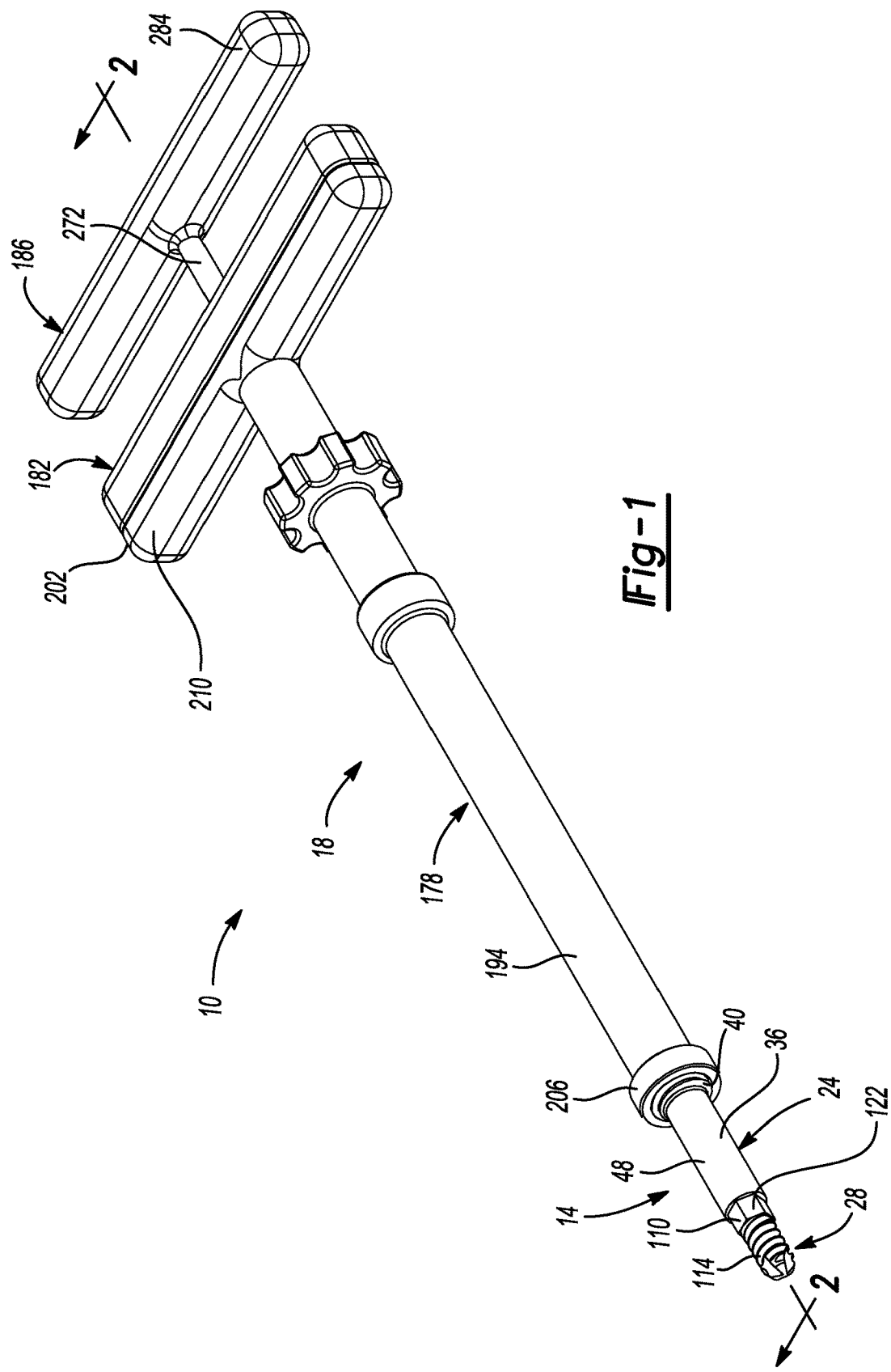
FIG. 1 is a perspective view of an exemplary fracture fixation system having an exemplary fastener assembly associated with an exemplary instrument assembly in accordance with various aspects of the present disclosure.

With particular reference to FIGS. 1-3, and continuing reference to FIGS. 4-5B, the exemplary instrument assembly 18 will now be discussed in greater detail. The exemplary instrument assembly 18 can include a first or outer cannulated drive instrument or member 178, a second or inner cannulated driver 182 and a third or internal driver 186. In the exemplary configuration illustrated, the first drive instrument 178 can include a cannulated body 194 having a proximal end 202 and a distal end 206. The cannulated body 194 can define a cannulated handle or torque generating feature 210 at the proximal end 202 and a cannulated shaft 214 extending therefrom to the distal end 206. The distal end 206 can include or define a proximal fastener member 24 coupling feature, such as internal threads 218, configured to threadably receive the external threads 60 of proximal head 40. In the exemplary configuration illustrated, the handle 210 can include a T-bar configuration 222 having an upper surface 226.

The second driver or drive member 182 can similarly include a cannulated body 234 having or defining a proximal end 238 and a distal end 242. The cannulated body 234 can include or define a cannulated handle or torque generating feature 246 at the proximal end 238 and a cannulated shaft 250 extending therefrom to the distal end 242. The distal end 242 can include or define a cannulated proximal fastener member 24 engaging feature 254, such as an external hexagon pattern, configured to removably and non-rotatably couple with the internal hexagon pattern 102 of the instrument coupling feature 80 of proximal head 40. In the example illustrated, the handle 246 can be sized and shaped to include a similar width as handle 210 in a direction perpendicular to shafts 214, 250. The handle 246 can also include a bottom side or surface 258 and an opposed upper side or surface 262. The cannulated shaft 250 can be sized and shaped to be telescopically received in cannulated shaft 214, as will be discussed in greater detail below.

The third driver or drive member 186 can also include a body 272 having or defining a proximal end 276 and a distal end 280. The body 272 can include or define a handle or torque generating feature 284 at the proximal end 276 and a shaft 288 extending therefrom to the distal end 280. The handle 284 can include a similar width as handles 210, 246 and can include a bottom surface 292. The shaft 288 can include or define an internal screw 32 engaging feature 296, such as an external hexagon pattern, configured to removably and non-rotatably couple with the internal hexagon pattern of the instrument coupling feature 168 of proximal head 152. The shaft 288 can also include a diameter sized to be movably received in the cannulated body 234 of second driver 182.

With continuing reference to FIGS. 1-3, assembly and general operation of the instrument assembly 18 will now be discussed in greater detail. As briefly discussed above, the second driver 182 can be inserted into the first drive instrument 178 and the third driver 186 can be inserted into the second driver 182, as generally shown in FIGS. 1 and 2 with reference to the exploded view in FIG. 3.

In one exemplary configuration and technique, the first drive instrument 178 can be removably threadably coupled to the proximal fastener member 24 via the respective external and internal threads 60, 218. The second driver 182 can be inserted into the first drive instrument 178 such that the proximal member engaging feature 254 can removably engage the instrument coupling feature 80 of proximal head 40 and the bottom side 258 of handle 246 can contact the upper side 226 of handle 210. In this regard, and as will be discussed in greater detail below in connection with an exemplary surgical technique, the handles 210, 246 can engage each other so as facilitate operation in unison, as shown for example in FIG. 1. As will also be discussed in greater detail below, the first drive instrument 178 and second driver 182 can be coupled to the fastener assembly 14 in the manner discussed above and utilized together to insert the fastener assembly 14 into bone so as to prevent relative motion of the fastener assembly components and/or premature compression of fastener assembly 14.

The third driver 186 can be inserted into the second driver 182 at the appropriate time (discussed below) to rotate the internal screw 32 to facilitate compression of the fractured bone(s). In this regard, in the exemplary configuration illustrated in FIGS. 1 and 2, the shaft 288 of the third driver 186 can include an axial length sized such that when the internal screw coupling feature 296 engages the corresponding feature 168 of internal fastener member 32, the handle 284 is spaced apart from the handle 246. In one exemplary implementation, the bottom surface 292 of handle 284 is spaced apart from the upper side 262 of handle 246, as shown for example in FIGS. 1 and 2.

In accordance with various aspects of the present teachings, the fracture fixation system 10 can be provided as part of a kit or in kit form. In this exemplary aspect, the kit can include the instrument assembly 18 and one or more fastener assemblies 14. In one exemplary implementation, the kit can include various fastener assemblies 14, with some assemblies 14 being the same and other assemblies having varying length proximal fastener members 24, distal fastener members 28, and corresponding varying length internal screws 32.

Turning now to FIGS. 6-9 and with continuing reference back to FIGS. 1-5B, an exemplary fracture fixation method or technique utilizing fracture fixation system 10 will now be discussed in greater detail. It will be appreciated that while the discussion will continue with reference to the fracture fixation system 10 being utilized for fracture fixation of an exemplary intercondylar fracture, the system and method discussed herein is applicable to various different bones and/or fractures thereof.

Figure 6:
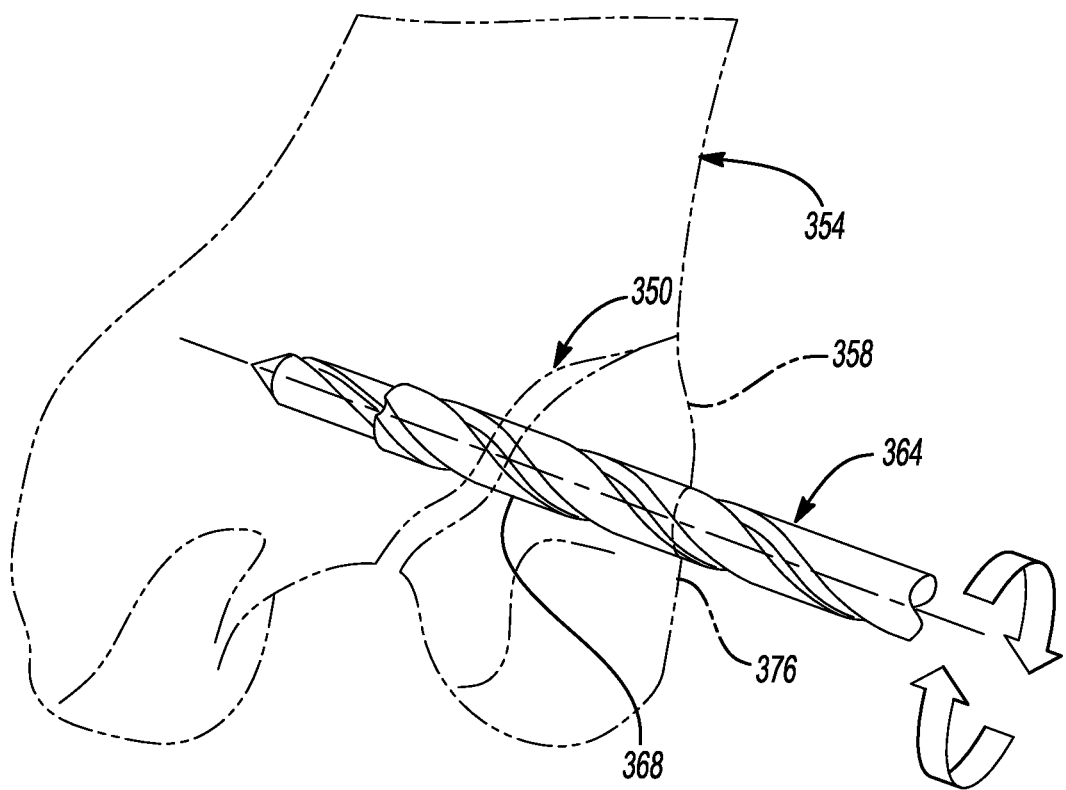
FIGS. 6-9 depict an exemplary method of using the instrument assemblies and fastener assemblies for fracture fixation according to various aspects of the present disclosure.

With initial reference to FIG. 6, an exemplary intercondylar fracture 350 of an exemplary femur 354 is shown. As briefly discussed above, the telescoping nature of the fastener assembly 14 can provide for the ability to provide sufficient compression of the intercondylar fracture 350 such that, in one exemplary technique, one or more fastener assemblies 14 can be inserted into one or more bone holes formed only from the lateral side 358. As can be appreciated by those skilled in the art, this exemplary technique can provide for improved access and reduced time in the operating room as compared to systems and methods that require medial and lateral access for compression of a fracture site.

With continuing reference to FIG. 6, an exemplary drill 364 is shown and can be utilized to form a hole in the femur 354 for receiving the fastener assembly 14. In the exemplary implementation illustrated, the drill 364 can include a stepped configuration corresponding to an external geometry of the fastener assembly 14. The drill 364 can be driven by any suitable means and can be advanced such that it forms a bone hole 368 through or relative to the fracture 350, as shown for example in FIG. 6. In one exemplary aspect of the technique, the drill can be driven from the lateral side 358 up to the medial cortical bone of the femur 354.

Once the bone hole 368 has been formed, an appropriately sized fastener assembly 14 can be selected, such as from the kit discussed above. The selected fastener assembly 14 can be removably coupled to the first drive instrument 178 and the second driver 182 in the manner discussed above and shown in FIG. 7. For clarity of discussion, the first drive instrument 178 and the second driver 182 coupled together and to the fastener assembly 14 in the manner discussed above and shown in FIG. 7 can hereinafter be referred to as the "first assembled configuration." In an exemplary aspect of the technique, the fastener assembly 14 can be positioned, before insertion into the bone hole 368, in an extended configuration where the distal fastener member 28 is extended to an approximate fully extended position relative to proximal fastener member 24 to provide for suitable retraction and thus compression. For example, as can be seen in FIG. 7, the proximal end 132 of distal fastener member 28 is positioned toward the distal end 52 of proximal fastener member 24.

Figure 7:
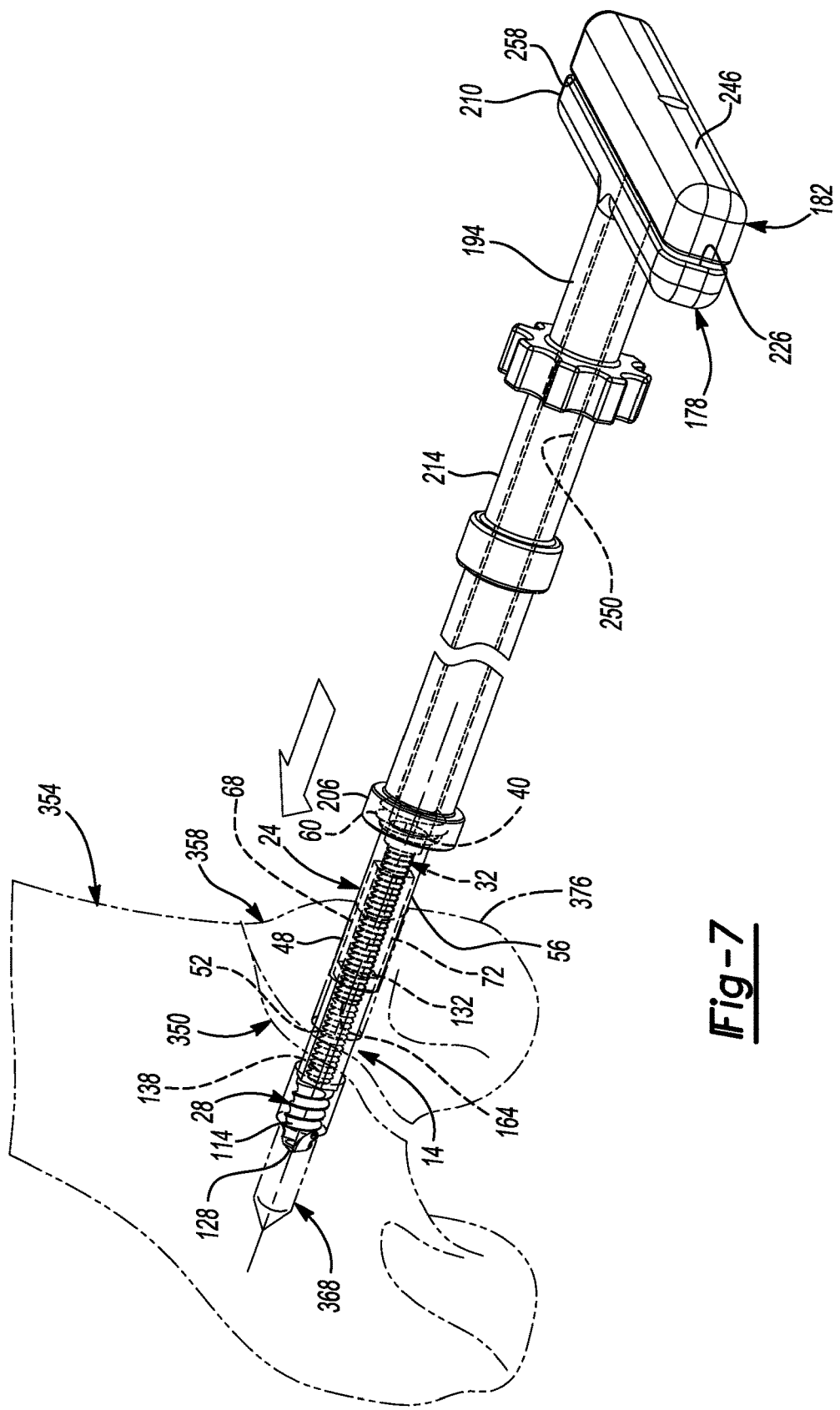

With the instrument assembly 18 in the first assembled configuration coupled to the fastener assembly 14 in its extended position, the instrument assembly 18 can be advanced toward femur 354 to advance the fastener assembly 14 into bone hole 368, as also shown in FIG. 7. As mentioned above, the handles 210, 246 can be operated in unison to both axially and rotationally advance fastener assembly 14 into bone hole 368. In one exemplary implementation, the distal end 242 of the second driver 182 can prevent the internal screw member 32 and thus the distal fastener member 28 from compressing or retracting during axial advancement of the fastener assembly 14. Upon advancing fastener assembly 14 an appropriate distance into bone hole 368, the handles 210, 246 can be rotated in unison to threadably advance the fastener assembly 14 into the bone hole until the fastener assembly 14 is fully seated. Turning both handles in unison can prevent unintended movement of components of fastener assembly 14, such as premature compression from such movement. In the exemplary technique illustrated, the fastener assembly 14 can be fully seated when the proximal head 40 is seated against an exterior 376 of the femur 354, as shown for example in FIG. 8.

Once the fastener assembly 14 is seated against the exterior 376 of the femur 354, the third driver 186 can be inserted into the cannulated second driver 182 as discussed above and shown in FIG. 9. In the exemplary technique illustrated, the third driver 186 can be inserted as shown such that the internal screw coupling feature 296 extends through and beyond the first drive instrument 178, second driver 182 and the proximal head 40, and into the internal coupling feature 168 of internal screw 32.

Figure 9:
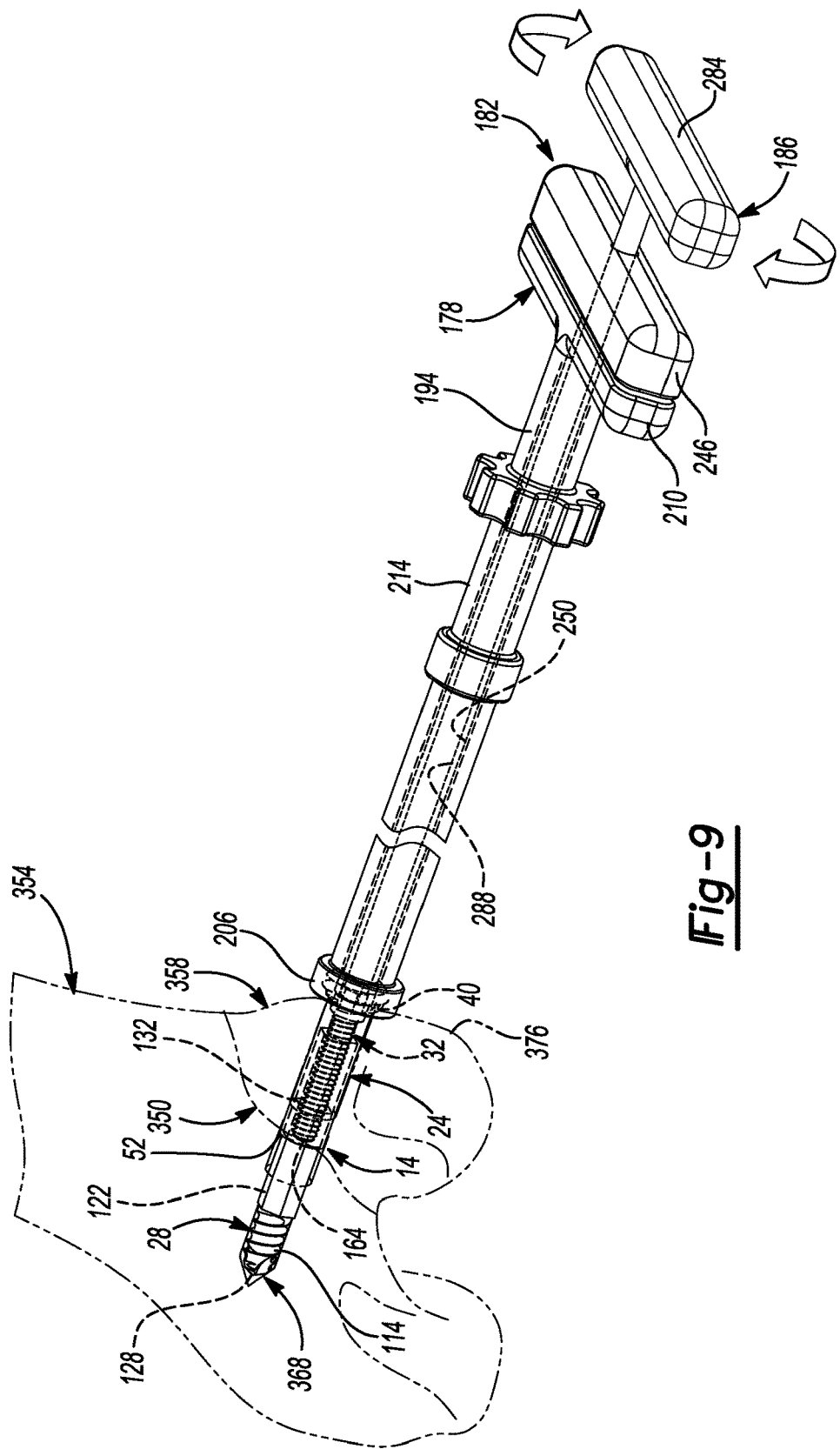

With the third driver 186 inserted and non-rotatably coupled to the internal screw member 32, the third driver 186 can be rotated, such as via handle 284, to retract the distal fastener member 28 telescopically into the proximal fastener member 24 to compress fracture 350, as shown for example in FIG. 9. During such rotation of third driver 186, the handles 210, 246 can be held to prevent any rotation of the proximal and distal fastener members 24, 28. As discussed above, clockwise rotation of the internal screw member 32 relative to the proximal and distal fastener members 24, 28, axially advances the distal fastener member 28 toward the head 40 of proximal fastener member 24 due to the cooperating anti-rotation features 72, 122.

Once appropriate compression of fracture 350 is achieved in the manner discussed above, the third driver 186 can be removed from the fastener assembly 14 and the first drive instrument 178 and the second driver 182. The first drive instrument 178 can then be unthreaded from the proximal head 40 via handle 210 while holding handle 246 to prevent unintended rotation of the fastener assembly 14. Once the first drive instrument 178 is unthreaded, the first drive instrument 178 and second driver 182 (if still positioned in the first drive instrument 178) can be removed from the fastener assembly 14.

Turning now to FIGS. 10-11 and with continuing reference to FIGS. 1-9, an alternative fracture fixation system is shown and generally identified at reference numeral 10'. Fracture fixation system 10' can include a fastener assembly 14' and an instrument assembly 18'. Fracture fixation system 10' can be similar to fracture fixation system 10 such that only differences between fastener and instrument assemblies 14', 18' and the fastener and instrument assemblies 14, 18 will be discussed below in detail, where like reference numerals refer to like or similar features.

In the exemplary implementation illustrated in FIG. 10, the fastener assembly 14' can include the distal fastener member 28, a proximal fastener member 24' and an internal fastener member 32'. In one exemplary implementation, the proximal fastener member 24' can be the same or substantially the same as proximal fastener member 24 except for the incorporation of a retention arrangement 380. Retention arrangement 380 can include one or more apertures 384 positioned in the cannulated shaft 48 and one or more retention members 388 configured to be positioned therein and engage a coupling feature 392 (discussed below) of the internal fastener member 32'. In the exemplary implementation illustrated in FIG. 10, the one or more apertures 384 include two diametrically opposed apertures 384 positioned proximate the head 40 and configured to receive corresponding retention members or pins 388. The retention arrangement 380 can be configured to retain internal fastener member 32', and thus the distal fastener member 28 threadably coupled thereto, relative to proximal fastener member 24, as will be discussed in greater detail below. In addition, in this exemplary implementation, the head 40 can be provided without external threads 60.

The internal fastener member 32' can also be the same or substantially the same as internal fastener member 32 except for the coupling feature 392 defined by proximal head 152'. As discussed below in greater detail, the coupling feature 392 can be configured to cooperate with retention arrangement 380 to retain an axial or longitudinal position of internal fastener member 32' relative to proximal fastener member 24'. In the exemplary implementation illustrated in FIGS. 10-11, the coupling feature 392 can include an annular recess or groove configured to receive a portion of the retention pins 388 therein to retain proximal fastener member 32' in the proximal fastener member 24' and against or substantially against the bearing surface 92. It will be appreciated that the retention arrangement 380 and coupling feature 392 cooperate to axially retain the internal fastener member 32' while allowing rotation of the fastener member 32' relative to the proximal and distal fastener members 24' and 28.

With particular reference to FIG. 10, the exemplary instrument assembly 18' will now be discussed in greater detail in connection with the fastener assembly 14'. As mentioned above, instrument assembly 18' can be similar to instrument assembly 18. In the example illustrated, instrument assembly 18' can be substantially the same as instrument assembly 18 without the first drive instrument 178. In other words, instrument assembly 18' can include only the second and third drivers 182, 186 because the retention arrangement 380 and cooperating coupling feature 392 can prevent any undesired compression of the fastener assembly 14' and thus remove a need for the interaction of the first drive instrument 178 and second driver 182 to prevent such undesired compression of fastener assembly 14'.

Figure 8:
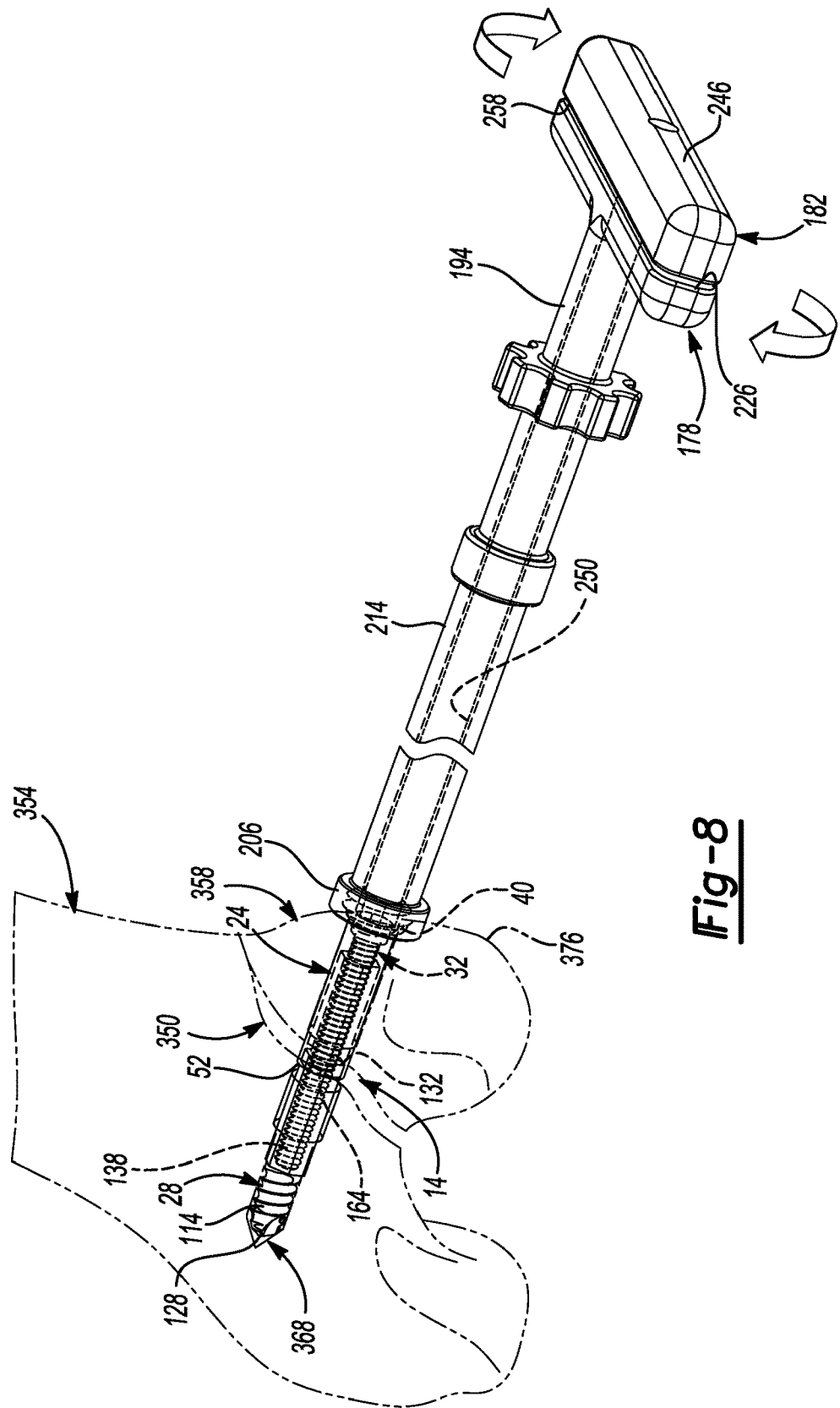

With continuing reference to FIGS. 10-11 and reference back to FIGS. 1-9, the fastener assembly 14' can be utilized in the same or substantially the same manner and in the same or substantially the same surgical technique(s) as those discussed above with particular reference to the exemplary technique discussed with reference to FIGS. 6-9. In this regard, the instrument assembly 18' can be utilized in a similar manner as with the technique discussed above, but without the first drive instrument 178 of instrument assembly 18. In particular, as discussed above, the instrument assembly 18' utilizes the second and third drivers 182, 186 and eliminates a need for the first drive instrument 178 based on the retention arrangement 380. As a result, the fastener assembly 14' can be advanced into the bone hole 368 and seated against the exterior 376 of the femur 354 in the same manner as discussed above, but utilizing only the second driver 182. Once the fastener assembly 14' is fully advanced and seated, such as shown in FIG. 8 for fastener assembly 14, the technique can continue with fracture fixation system 10' in the same manner as discussed above for fracture fixation system 10.

Turning now to FIG. 12 and with continuing reference to FIGS. 1-11, the fracture fixation systems 10 and 10' can include and/or be utilized with one or more bone plates, such as the exemplary bone plate 396 shown in FIG. 12. In this regard, it will be appreciated that the exemplary technique and systems discussed above with reference to FIGS. 1-11 can be utilized in the same or substantially similar manner with exemplary bone plate 396. When bone plate 396 is utilized, the procedure can alternatively include seating the fastener assemblies' proximal head 40 against the bone plate 396 instead of the exterior 376 of femur 354. It will also be appreciated that, while not specifically shown, the bone plate can also be utilized with other screws, such as locking screws and/or poly-axial screws.

Turning now to FIG. 13, the fracture fixation systems 10 and 10' can include and/or be utilized with one or more orthopedic fixation systems. In the illustrated example, the fastener assemblies 14 and 14' are shown in use with an exemplary orthopedic fixation system 400, such as a retrograde intramedullary nail. The intramedullary nail 400 can be used to repair damaged tissue in an anatomy, such as a fracture between a femoral head 404 and the femur 354. A more detailed discussion of intramedullary nail 400 can be found in U.S. Pat. No. 8,394,103 assigned to Biomet Manufacturing, LLC. Briefly, however, the intramedullary nail 400 can be used with one or more reconstructive orthopedic fasteners, such as reconstructive screws (not shown) to couple the femoral head 404 to the femur 354 via the engagement of the reconstructive screws with the intramedullary nail 400. Fixation screws can secure the intramedullary nail 400 distally to the femur 354, and can provide additional stability. In lieu of or in addition to the fixation screws mentioned above, the fastener assemblies 14 and 14' can be used to secure the intramedullary nail while also compressing an exemplary fracture 350.

In this regard, the intramedullary nail 400 can include an internal bore 408 and a locking system 412 received therein. The locking system 412 can comprise any suitable system capable of securing the fixation screws and/or the fastener assemblies 14, 14' to the intramedullary nail 400, such as the CORELOCK™ locking system commercially available from Biomet, Inc. of Warsaw, Ind., and described in commonly-owned in U.S. patent application Ser. No. 12/183,142, filed on Jul. 31, 2008, and incorporated by reference herein. Thus, the locking system 412 will not be described in great detail herein. Briefly, however, the locking system 412 can be positioned within a distal end of the retrograde intramedullary nail 400 such that the fixation screws and/or fastener assemblies 14, 14 can pass through the locking system 412 and throughbores of the retrograde intramedullary nail 400, so that the locking system 412 can secure the fixation screws and/or fastener assemblies 14 to the retrograde intramedullary nail 400. In the example illustrated, the outer cylindrical surface 56 of proximal fastener member 24 can pass through the throughbores and the locking system 412 of intramedullary nail 400, as shown in FIG. 13.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A fastener assembly for use with fracture fixation, comprising:
   a cannulated proximal fastener member having a proximal fastener head configured to be seated on an exterior side of a bone, an opposed distal end and an internal wall defining an internal keyed anti-rotation feature and having an exterior wall defining a diameter, wherein a diameter of the head is larger than the diameter of the exterior wall such that the head has a lower surface configured to be seated against an exterior bone surface or a bone plate;
   a distinct distal fastener member having a proximal end defining an internal bore and an external keyed anti-rotation feature, and a distal end defining a bone anchor; and a distinct internal fastener member configured to be positioned in the proximal fastener member and threadably coupled to the distal fastener member such that the proximal end of the distal fastener member is telescopically received in the distal end of the proximal fastener member;

wherein rotation of the internal fastener member in a first rotational direction telescopically retracts the distal fastener member into the proximal fastener member so as to be adapted to compress a bone fracture, and rotation of the internal fastener member in a second opposite rotational direction extends the distal fastener member relative to the proximal fastener member, and further comprising a retention arrangement including one or more pins mounted to the proximal fastener member that engage a groove around a head of the internal fastener member and are configured to prevent axial movement of the internal fastener member relative to the proximal fastener member while allowing relative rotational movement of the internal fastener member.

2. The fastener assembly of claim 1, wherein the internal and external anti-rotation features have complementary respective internal and external surfaces.

3. The fastener assembly of claim 2, wherein the complementary internal and external surfaces include one of respective internal and external hexagon or partial hexagon patterns in cross-section configured to permit relative axial movement and prohibit relative rotational movement.

4. The fastener assembly of claim 2, wherein the proximal fastener head defines external threads adapted to removably receive an instrument inserter member, and an internal drive engagement feature adapted to removably receive a drive instrument; and wherein the bone anchor of the distal fastener member comprises external threads.

5. The fastener assembly of claim 4, wherein the internal shoulder and bearing surface are positioned distally of the internal drive engagement feature such that the internal screw head is positioned distally of the internal drive engagement feature.

6. The fastener assembly of claim 1, wherein the proximal fastener member defines an internal shoulder having a bearing surface; and wherein the internal fastener member comprises an internal screw having a screw head configured to engage the bearing surface.

7. The fastener assembly of claim 6, wherein the internal screw comprises a threaded shank and wherein the internal bore of the distal fastener member comprises internal threads such that the threaded shank of the internal screw member threadably couples the proximal fastener member to the distal fastener member.

8. The fastener assembly of claim 7, wherein the internal bore comprises a blind internal bore.

9. A fastener assembly for use with fracture fixation, comprising:

a cannulated proximal fastener member having a proximal fastener head configured to be seated on an exterior side of a bone, an opposed distal end and an internal wall defining an internal keyed anti-rotation feature, the internal keyed anti-rotation feature including at least one planar surface;

a distinct distal fastener member having a proximal end defining an internal bore and an external keyed anti-rotation feature, and a distal end defining a bone anchor, the external keyed anti-rotation feature including at least one planar surface corresponding to the at least one planar surface of the internal keyed anti-rotation feature; and a distinct internal fastener member configured to be positioned in the proximal fastener member and threadably coupled to the distal fastener member such that the proximal end of the distal fastener member is telescopically received in the distal end of the proximal fastener member;

wherein rotation of the internal fastener member in a first rotational direction telescopically retracts the distal fastener member into the proximal fastener member so as to be adapted to compress a bone fracture, and rotation of the internal fastener member in a second opposite rotational direction extends the distal fastener member relative to the proximal fastener member, and further comprising a retention arrangement including one or more pins mounted to the proximal fastener member that engage a groove around a head of the internal fastener member and are configured to prevent axial movement of the internal fastener member relative to the proximal fastener member while allowing relative rotational movement of the internal fastener member.

10. The fastener assembly of claim 9, wherein the internal and external keyed anti-rotation features include one of respective internal and external hexagon or partial hexagon patterns in cross-section configured to permit relative axial movement and prohibit relative rotational movement.

11. The fastener assembly of claim 9, wherein the proximal fastener member defines an internal shoulder having a bearing surface; and wherein the internal fastener member comprises an internal screw having a screw head configured to engage the bearing surface.

12. The fastener assembly of claim 11, wherein the internal screw comprises a threaded shank and wherein the internal bore of the distal fastener member comprises internal threads such that the threaded shank of the internal screw member threadably couples the proximal fastener member to the distal fastener member.

13. The fastener assembly of claim 12, wherein the internal bore comprises a blind internal bore.

* * * * *